United States Patent [19]
Babson et al.

[11] Patent Number: 5,721,141
[45] Date of Patent: Feb. 24, 1998

[54] TUBE WASHING SYSTEM

[75] Inventors: Arthur L. Babson, Chester; Thomas Palmieri, Paramus, both of N.J.

[73] Assignee: DPC Cirrus Inc., Randolph, N.J.

[21] Appl. No.: 670,996

[22] Filed: Jun. 28, 1996

[51] Int. Cl.$^6$ ............................. G01N 1/28; G01N 35/10
[52] U.S. Cl. ...................... 436/49; 436/43; 436/47; 436/174; 436/177; 436/180; 422/63; 422/65; 422/72; 422/100; 422/101; 134/150; 134/157
[58] Field of Search .................. 436/43, 45, 47, 436/48, 49, 174, 177, 180, 175; 422/63, 64, 65, 68.1, 72, 99, 100, 101, 103, 104; 134/33, 34, 148, 150, 157, 186

[56] References Cited

U.S. PATENT DOCUMENTS

| 3,151,073 | 9/1964 | Anton | 422/72 |
|---|---|---|---|
| 4,053,284 | 10/1977 | Posch | 23/259 |
| 4,323,537 | 4/1982 | Mody | 422/63 |
| 4,879,242 | 11/1989 | Tsukioka | 436/54 |
| 4,895,453 | 1/1990 | Devlin et al. | 366/219 |
| 5,316,726 | 5/1994 | Babson et al. | 422/65 |

OTHER PUBLICATIONS

Trade Brochure, entitled "PK310 Fully Automated Enzyme Analyser", a publication of Olympus Biomedical Products Div., Wendenstrasse 14–16, 2 Hamburg 1, Germany, 15 pages, undated.

*Primary Examiner*—Long V. Le
*Attorney, Agent, or Firm*—Whitham, Curtis, Whitham & McGinn

[57] ABSTRACT

A tube washing system including a tube spinning station having a rotatable chuck and a waste chamber surrounding the chuck for capturing and draining tube fluids expelled from a spun tube driven in rotation by the chuck. The chuck has a body portion and a plurality of spaced apart teeth defining intervening grooves extending through the body portion with at least one of the grooves permitting passage of fluid through the body portion and at least one other of the grooves receives and mechanically connects a projection on an open end of a tube. A pipette for dispensing wash water into a tube is located centrally within the chuck. There is also a tube elevating device located beneath the tube spinning station, the tube elevating device comprising a freely rotatable tube holder, and lift drive motor provided to vertically move the tube holder towards and way from the chuck. The tube used in the washing system has at least one projection provided on its open end which can interlock with a chuck groove. The invention also relates to a method of using the tube washing system to rapidly and efficiently wash a tube and its contents.

9 Claims, 6 Drawing Sheets

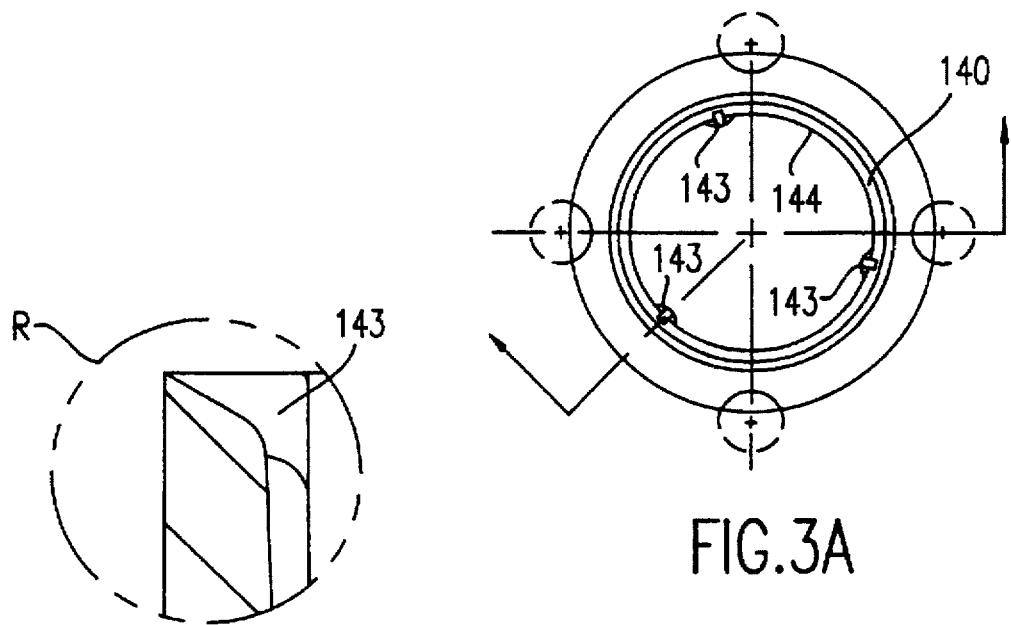
FIG.3A
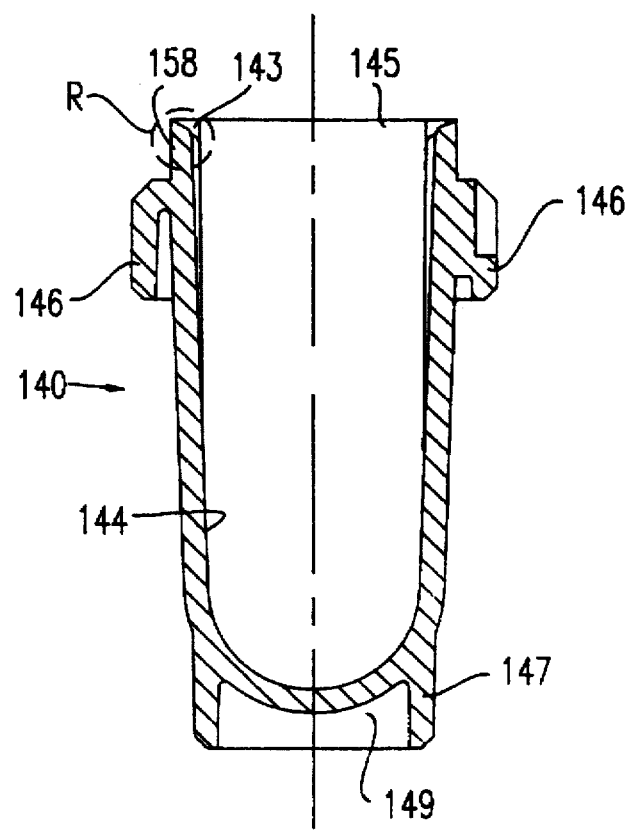
FIG.3B
FIG.3

TUBE WASHING SYSTEM

BACKGROUND OF THE INVENTION

1. Field of the Invention

The invention is generally relates to a tube washing system, and the tube washing system being particularly well-suited for the washing of tube contents in an automated chemical or immunoassay analyzer.

2. Description of the Prior Art

An immunoassay is a well known laboratory method used to determine the amount of an analyte in a sample such as plasma or urine. It is based on the interaction of antibodies with antigens, and because of the degree of selectivity for the analyte (either antigen or antibody), an immunoassay can be used to quantitatively determine very low concentrations of drugs, hormones, polypeptides, or other analyte compounds found in a test sample. For many years, immunoassays were performed by hand by trained laboratory technicians.

Recently, many companies have begun producing automated immunoassay analyzers. Automating the immunoassay procedures can be onerous because of the large number of steps needed to be executed. For example, in a conventional scheme, a sample is mixed with a reagent and a solid support having a bound antigen or antibody, the sample is incubated such that the corresponding antigen or antibody in the sample and a labeled antigen or antibody provided in the reagent can be bound to the antigen or antibody on the solid support, then the solid support is thoroughly washed and the label (fluorescent, radioactive, chemiluminescent, or the like) is detected by an appropriate mechanism, and finally the analyte of interest (antigen or antibody) is quantified from the detected label.

Most of today's automated immunoassay analyzers are designed for "walk away" operation, where the technician loads sample containing tubes onto a carousel and presses a start button. Thereafter, the automated immunoassay analyzer mixes appropriate reagents (often stored aboard the analyzer) with the sample, performs incubating and washing operations, detects the label, and computes the quantity of analyte in the sample from the detected label and stored calibration curves. The entire operation is typically done under computer control, and in some automated immunoassay analyzers, bar coding is used to identify the sample under test. The results of the immunoassays are typically output onto computer paper for inspection by the technician, or monitored and displayed in real time as described in U.S. Pat. No. 5,316,726.

One of the chief stumbling blocks for performing the automated immunoassay has been the step of thoroughly washing the solid support. In immunoassays, it is imperative that the free label and bound label be completely separated prior to detection of the bound label or erroneous results will occur. Many of today's automated immunoassay analyzers utilize high speed pipetting and aspirating stations for the washing operation. Pipetting and aspirating wash fluid into and out of a sample container requires a large number of mechanized parts. Moreover, it is very difficult to completely remove all sample and wash fluid from a reaction chamber via aspiration; therefore, an automated system which uses such a wash station can be susceptible to various detection errors.

U.S. Pat. No. 5,316,726 describes an approach to overcome such problems associated with such conventional tube washing schemes. In particular, U.S. Pat. No. 5,316,726 describes use of an assay tube having a special configuration wherein a waste chamber (or apron) is arranged concentrically around the exterior of an upper end of a central assay tube containing, at its base, the bound biomaterial on an inert support. For washing operations, the assay tube with such a waste chamber is fitted with a cover over the top of the assay tube to contain sprayed sample fluid during high speed rotation, and then the assay tube is subjected to high speed spinning, whereby the sample fluid creeps up an outwardly tapered inside wall of the central tube under centrifugal forces and is sprayed outwardly over the top of the central tube to be collected in the waste chamber. The high speed spinning in U.S. Pat. No. 5,316,726 is described as involving a high speed spin station comprised of a high speed driver and an idler. The cover is adapted to permit penetration by a pipette tip or has a small diameter hole of smaller diameter than the top end of the central tube to allow introduction of wash water into the central tube, and high speed rotation of the assay tube is again used to remove the introduced wash water from the central tube with its capture occurring in the encircling integral waste chamber basin (or apron). Successive additions of wash water and spin removal of each can be practiced using the assay tube with an integral waste water chamber described in U.S. Pat. No. 5,316,726 to allow the wash operation to be performed more quickly and with higher precision than by aspiration techniques. The waste chamber typically can only hold small amounts of wash fluid, e.g., about 1.8 ml. This limitation requires repeated and interrupted wash steps to be performed. Otherwise, if the holding capacity of the waste chamber is exceeded, the excess wash fluid undesirably will be flung into the surrounding work area. After such washing, the assay tube and inert support of U.S. Pat. No. 5,316,726 will be free of unbound labeled reagent so that only bound labeled reagent will be detected. The washed assay tubes of U.S. Pat. No. 5,316,726 are then transferred to a detection station for quantification of the analyte of interest.

SUMMARY OF THE INVENTION

It is an object of this invention to provide an improved tube washing system.

It is another object of the invention to provide a tube washing system which allows a wash operation to be performed rapidly and with high precision in wash water removal.

According to the invention, an improved tube washing system is provided with a high speed spinning station having a chuck housed within and surrounded by a waste chamber, where the waste chamber serves as a receptacle for collecting and draining wash water fluid spun out of a tube. The drive chuck has a plurality of spaced apart teeth defining intervening grooves. The waste chamber is a water-tight enclosure other than for a drainage port and an aperture defined in its lower side having a size effective to receive a tube. The tube has at least one vertically extending, lineal ridge provided on the inner surface of the tube, where the ridge(s) is sized to permit sliding into a chuck groove presented between a pair of neighboring chuck teeth to thereby mate the tube ridge(s) with a chuck groove to provide a means of temporarily physically and mechanically interlocking the tube and chuck. The tube can be lifted vertically via tube elevating means to pass through the chamber aperture to enter the chamber to an extent where at least one such tube ridge slides into a chuck groove. Once the tube is elevated into the chamber effective to mechanically interlock with the chuck via mating of at least one tube ridge and chuck groove, the tube is rotated on its vertical axes by driving the chuck in rotation while supporting the bottom of the tube on a freely rotatable holder, thereby expelling fluids from the tube into the waste chamber through unmated grooves in the chuck, while allowing the retention of any immunoreceptive bead held within the tube. When rotation ceases, the expelled waste fluids drain by gravity into the lower basin of the waste chamber and are withdrawn. Washing is accomplished by the addition of water to the tube during, or followed by, centrifugation.

In the present invention, the waste chamber does not have to be incorporated into the tube structure itself, as the high speed spinning station structurally temporarily lends a waste chamber to the tube during its centrifugation and washing. Also, due to the enclosed waste chamber, the volume of wash fluid used is not limited by any volume capacity of an apron or sump formed on the tube structure; instead any overflow wash fluid is captured and drained by the waste chamber enclosure.

BRIEF DESCRIPTION OF THE DRAWINGS

The foregoing and other objects, aspects and advantages will be better understood from the following detailed description of the preferred embodiments of the invention with reference to the drawings, in which:

FIG. 3 is an enlarged fragmentary cross-sectional side view of the assay tube used in the tube wash system of FIG. 1;

FIG. 3A is a top view of the assay tube of FIG. 3;

FIG. 3B is an enlarged view of encircled area R in FIG. 3;

DETAILED DESCRIPTION OF THE PREFERRED EMBODIMENTS OF THE INVENTION

The tube wash system of the present invention can be used as a subsystem of an analytical instrument intended to produce reportable assay results through the processing of specimens and various other components of the chemistry system. This processing involves the control and timing of various internal operations as well as the acquisition and processing of data generated internally or through interaction with an external computer system such as LIS. The analytic instrument is an integrated electromechanical apparatus which processes specimens in order to generate test results. It is comprised of all the mechanical hardware, electronic hardware and software required to perform chemical or immunoassays.

By way of example, the basic overall series of steps use to perform a immunoanalysis test on a sample of interest, including use of the tube washing system of this invention, is as follows:

a) deposition of reaction tubes onto a reaction tube load chain;

b) deposition of beads into reaction tubes using the inventive bead dispenser system;

c) transfer reaction tubes from reaction tube load chain to a pipetting station for depositing the specimen (analyte of interest) and liquid reagent into the reaction tube (already containing the bead);

d) incubation and agitation of reaction tubes;

e) washing of the incubated reaction tubes with a tube washing system of the present invention;

f) substrate (e.g., chemiluminescent) addition, incubation, or addition of trigger compounds;

g) quantitation of analyte (e.g., by reaction tube light output measurement); and h) discharge of spent tubes.

Figure 1:
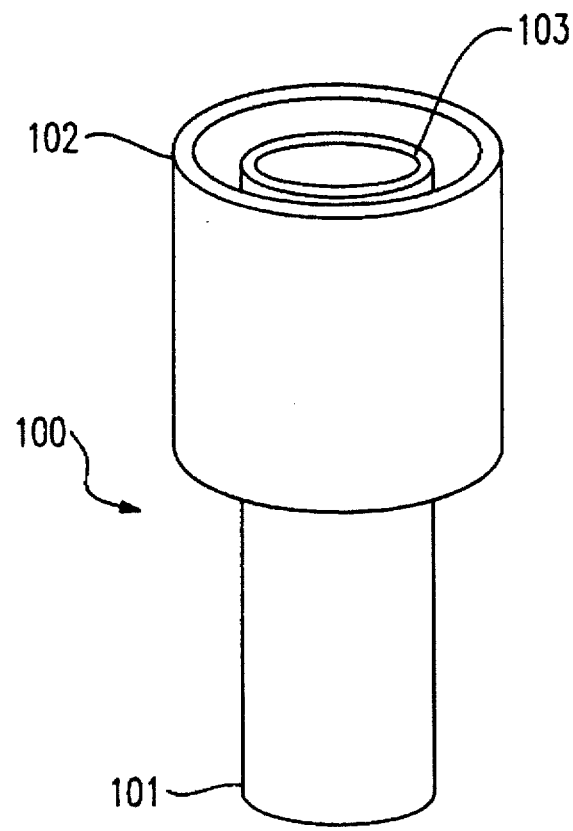
FIG. 1 is an isometric view of a conventional assay tube 100 construction of U.S. Pat. No. 5,316,726 having an integral waste chamber (apron) 102 formed at the top end 103 of a central tube 101 containing inert support bead 105 with bound biomaterial on its surface (seen in FIG. 1A)
Figure 1A:
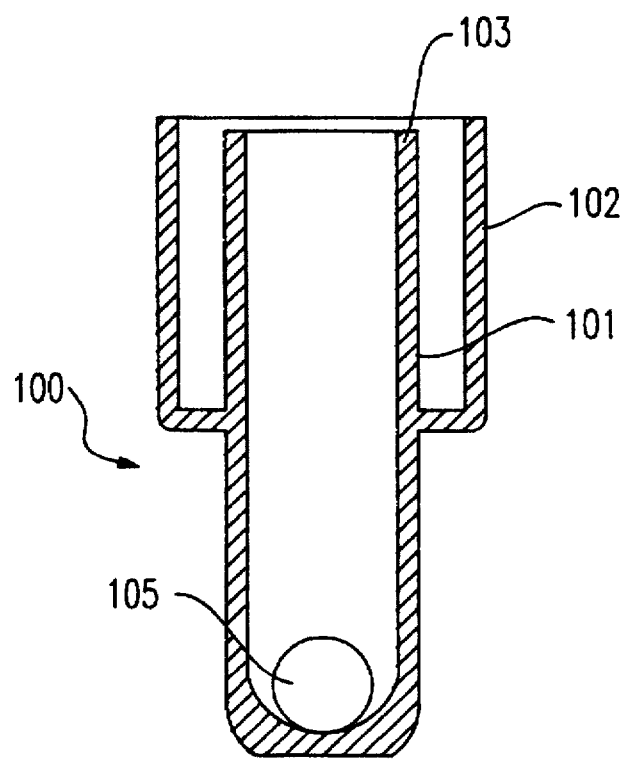
FIG. 1A is a cross-sectional side view of the conventional assay tube shown in FIG. 1.
Figure 2:
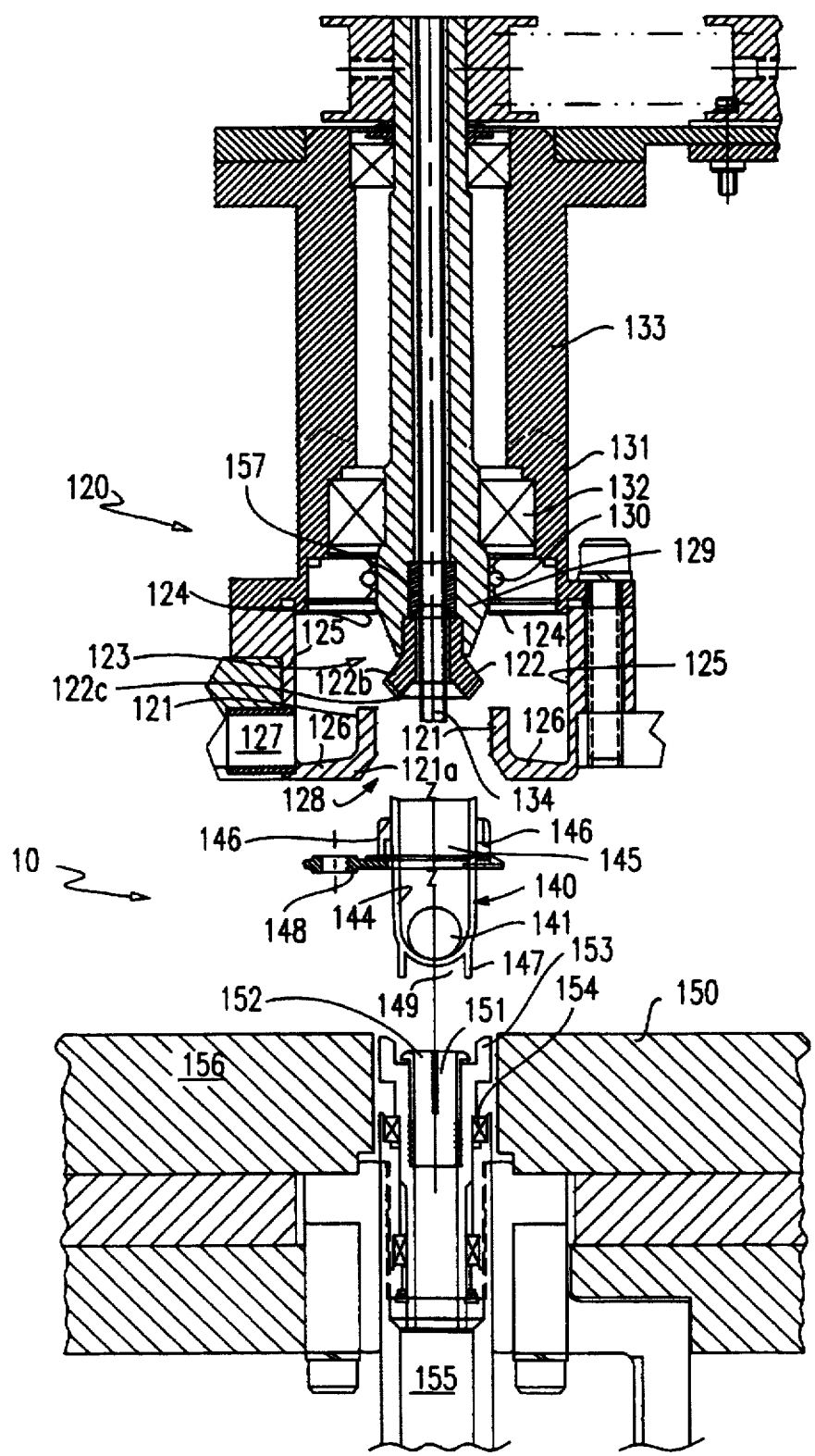
FIG. 2 is a cross-sectional side view of a tube wash system of the invention in a nonengaged status with an assay tube.
Figure 4:
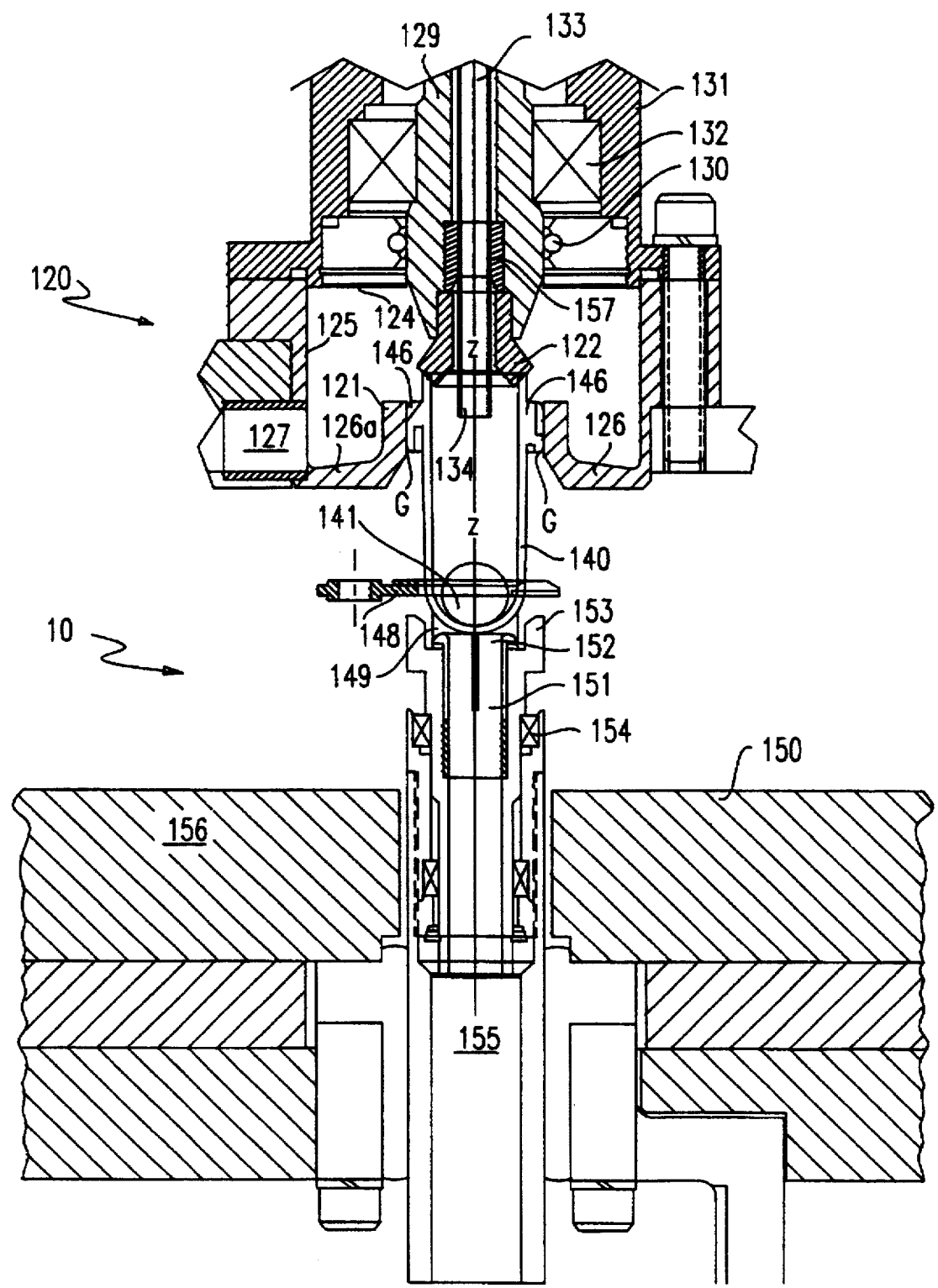
FIG. 4 is a cross-sectional side view of a tube wash system of the invention in an engaged status with an assay tube.

Referring now to the drawings, and more particularly to FIG. 2, there generally is shown a tube washing system 110 provided with a high speed spinning station 120 having an angled, grooved chuck 122 housed within and surrounded by a waste chamber 123. Further details on the configuration of chuck 122 will be developed hereinafter where suitable. In FIG. 2, the high speed spinning station 120 is shown in its nonengaged position relative to tube 140. When engaged, such as shown in FIG. 4, the waste chamber 123 serves as a receptacle for collecting and draining wash water fluid spun out of a tube 140. The waste chamber 123 is an enclosure defined by an upper surface 124, side wall 125, and a bottom surface 126 having an arcuate shape curving inward and upward near its center to define an aperture 128 bounded by upward projection 121. The aperture 128 has a size selected permit entry of tube 140. The port 127 communicates with a lower end of the chamber 123 to provide a means of drainage of wash water and other fluids expelled from the tube 140 during centrifugation and captured in waste chamber 123. As bottom surface 126 has upward curving projections 121, wash fluid that is expelled from a tube during spinning will strike chamber walls 124 and 125 and then drain by gravity out of port 127 without being able to climb up and over projections 121 at the bottom surface of the chamber 123. Therefore, wash fluid will not seep out of a small gap provided between tube 140 and the closely confronting, but noncontacting, inward surfaces 121a of projections 121. The opening 128 defined by chamber projections 121 is sized to provide a small circumferential gap G, e.g., about $12/1000$ inch clearance, between the inner surfaces of projections 121 and the continuous tube flange 146.

Figure 5:
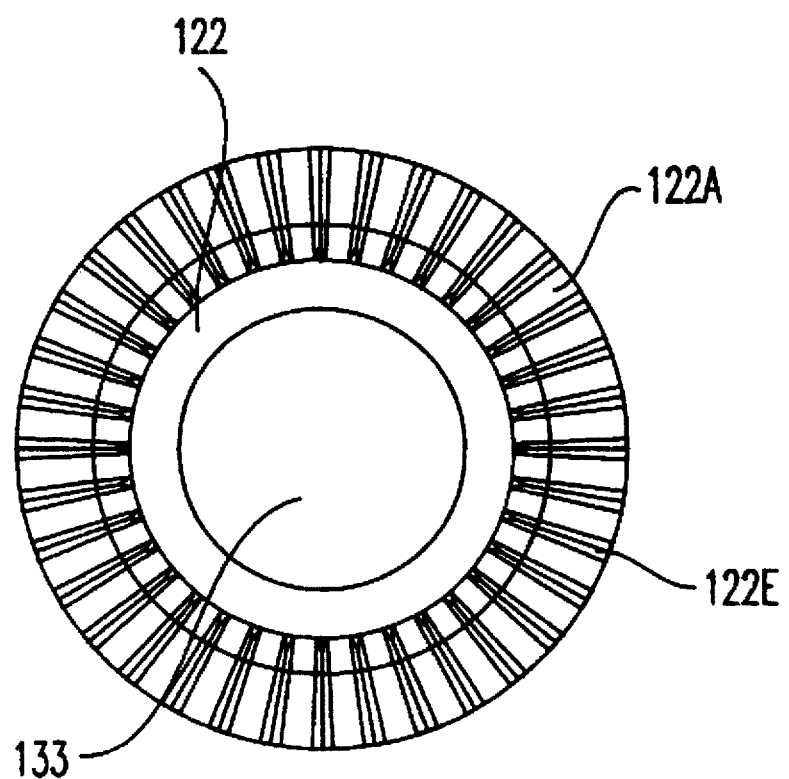
FIG. 5 is an enlarged bottom view of a drive chuck used in a high speed spinning station of a tube washing station of the invention.
Figure 6:
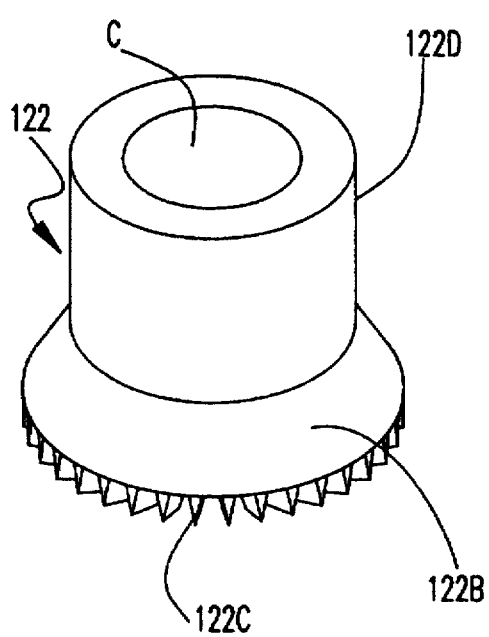
FIG. 6 is a top perspective view of the drive chuck of FIG. 5.

As more easily seen in FIG. 6, the chuck 122 preferably is a bevel gear has a body portion defined by an upper surface 122b of generally hemispherical-shape merging into upright stem 122d, and a grooved bottom surface 122c. As best seen in FIG. 5, the bevel gear 122 has alternating grooves or slots 122a and teeth 122e disposed around the entire circumference of bottom surface 122c. As seen in FIG. 6, the series of spaced apart teeth 122e and intervening grooves 122a angle up to hemispherical portion 122b at an angle, preferably an angle of about 45°. Chuck 122 also has a central throughhole "c" capable of receiving and allowing a pipette to be passed through the chuck. The chuck 122 also is formed of a rigid material, such as metal. The chuck 122 is mounted in shaft 129 for rotation and the chuck 122 distends through the top surface 124 to reside inside the waste chamber 123. The drive shaft 129 is sealed with an O-ring 130, and bearings 132 are provided between drive shaft 129 and support frame 131. The drive shaft 129 is driven to rotate about axis z-z by a spin motor (not shown).

A pipette 133 extends through drive shaft 129 and the center of chuck 122 and its dispensing tip 134 emerges from the bottom of chuck 122 a distance sufficient to permit the tip 134 to enter a tube 140 (once lifted into chamber 123 as seen in FIG. 4) without closely approaching or contacting the bead support 141. A solenoid wash pump (not shown) controllably delivers wash water volumes to pipette 133. The pipette 133 does not spin with chuck 122 due to the provision of bushing 157 around pipette 133. The bushing 157 can spin while maintaining pipette 133 in a centered non-spinning position.

The tube 140 to be washed has at least one projection or ridge 143 (best seen in FIG. 3A and FIG. 3B) upstanding from the inner surface 144 of the tube. Preferably, the ridge 143 gradually tapers in height and width downward from the upper rim 158 of the mouth 145 of tube 140 and disappears on the inner surface 144 as it approaches the inner bottom of the tube 140. The ridge(s) 143, at the rim area 158, is sized in inward projection and width dimensions sufficient to permit sliding of the ridge(s) 143 into a groove(s) 122a of chuck 122 and its nesting between two adjoining chuck teeth 122e. The inter-fit of the ridge 143 and chuck groove 122a preferably should be provided with close clearances as loose fits may cause wear on the ridges 143 or chuck teeth 122e.

For example, in the illustrations of FIGS. 3A and 3B, three ridges 143 have been provided on the inner surface 144 of test tube 140, which ridges can be nested between three pairs of teeth in chuck 122 to provide means of temporarily physically and mechanically interlocking the tube 140 and chuck 122 when the tube 140 is engaged (lifted into) chamber 123 such as shown in FIG. 4. Preferably a plurality of ridges 143, e.g. three or more, will be formed on the inner side 144 of the tube 140 as equidistantly spaced around the inner circumference of the tube 140. The ridges 143 preferably will have a draft angle of about 0.5°, while the tube surface 144 has a draft angle of about 2° to prevent nesting of the tube in a bulk hopper.

The number of ridges 143 will be less than the total number of grooves 122a provided in chuck 122. Therefore, at least one, and preferably a plurality, of grooves 122a will remain unobstructed by any ridge 143 of tube 140 during tube spinning, and thus remain available as escape paths for wash fluids being expelled from the tube 140 during spinning within the waste chamber 123.

The tube 140, at its bottom end, preferably is provided with a continuous circular sleeve 147 extending downward and defining a recess 149 in its bottom surface to permit handling by a lifting means holder, described in greater detail hereinafter. The tube 140, at its top end, preferably has a continuous flange means 146 provided on its outer side wall. The tube 140 is supported and oriented for alignment of tube ridges 143 with chuck grooves 122a by tube conveyor chain link 148 when the tube 140 is nonengaged (nonlifted) relative to the high speed spinning station 120, such as shown in FIG. 2.

To form the ridges 143 and continuous flange 146 integral with tube 140, tube 140 can be injection molded with styrene-butadiene copolymer, such as "KR03", commercially available from Phillips 66 Co, Bartlesville, Okla. 74004.

Figure 7:
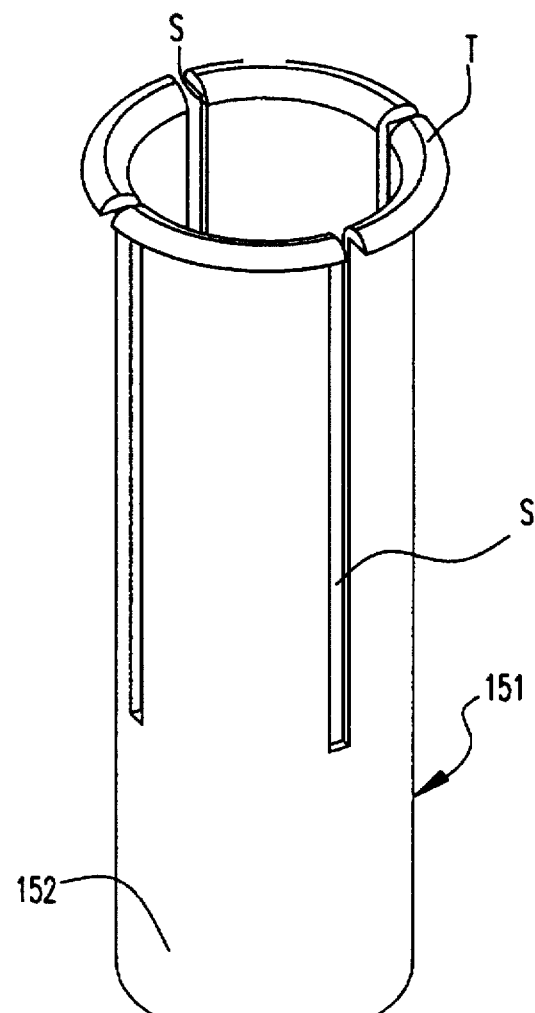
FIG. 7 is a top perspective view of a tube holder used to support the bottom of a test tube during its washing in a tube washing station of the invention.

The tube 140 is lifted (and retracted) vertically along the z-z axis direction via tube elevating means 150, such as shown in FIG. 2. Tube elevating means 150 includes a tube holder 151 which holds and retains tube 140 during lift of tube 140 into waste chamber 123. As shown in FIG. 7, the tube holder 151 is a hollow metal tube 152 divided at its upper half by four slots s extending from the top end t to about halfway down the length of tube 152. This defines four 90° quadrants at the top end t of tube 152 and the tube is flanged or hooked by bending outward at top end t. The tube 152 preferablly is beryllium-copper alloy, which provides good spring-like flexure properties. As seen in FIG. 4, the flanged top t of tube 152 interfits recess 149 of the bottom of the tube 140, such that posts 147 of tube 140 can slide over the outer flanged periphery at the top t the tube 152 with continuous circular tube holder sleeve 153 sliding in opposition over the outer sides of the tube posts 147. The flanged portion t of tube 152 is slightly oversized relative to recess 149 in tube 140 for positive retraction. The tube elevating means 150 includes bearings 154 permitting free rotation of the tube holder 151 relative to transfer block 156. The tube elevating means 150 further includes a reciprocal shaft 155, which is vertically moveable in the z-z axis direction, where the shaft 155 is connected to a lift motor (not shown). The lift motor, when actuated, will drive the shaft 155 vertically upward to interfit tube holder 151 with the bottom of tube 140, as supported and oriented by a chain link of a tube conveyor 148, and continue to lift the tube 140 to a height until it enters waste chamber 123 and tube ridge(s) 143 slides into and mate with chuck groove(s) 122a. At this point, as shown in FIG. 4, the tube 140 is engaged with high speed spinning station for washing and spinning. The flanges 146 of the tube 140 present an outer profile diameter that is less than the diameter of aperture 128 defined by bottom surface 126 of the waste chamber 123.

Once the tube 140 is so elevated into the chamber 123 effective to mechanically interlock with the chuck 122 via mating of tube ridge(s) 143 and chuck groove(s) 122a, the tube 140 is rotated on its vertical axes z-z by driving the chuck 122 in rotation while the tube is supported at the bottom of the tube (147, 149) via freely rotatable holder 151 which rotates as dictated by the movement of the chuck. During rotation, fluids are expelled from the tube 140 into the waste chamber 123 through the grooves 122a in the chuck 122, while allowing the retention of any immunoreceptive bead 141 held within the tube 140. For most wash applications, the tube spin rate will generally range from about 3,000 to about 10,000 rpm.

When rotation ceases, the expelled waste fluids drain by gravity into the lower basin 126a of the waste chamber 123 and are withdrawn for disposal via drainage port 127. Washing can be accomplished by the addition of water to the tube 140 during, or followed by, centrifugation. Wash water is added to the assay tube 140 via a solenoid wash pump (not shown) delivering volumes of wash water to pipette 133 which pipettes the volumes of water straight down into assay tube 140. Although not particularly limited to such, in a preferred operation, multiple 400 μL volumes of water (e.g. four) are pipetted into the assay tube 140. After each addition, the wash water is almost instantaneously removed after washing the inert support 141 with the bound biomaterial by high speed rotation of the tube 140.

Once the washing and centrifugation are completed for a given tube 140, the tube can be lowered via the tube elevating means 150 by retracting its shaft 155 with the tube ridge(s) 143 sliding back out of the chuck groove(s) 122a and the tube 140 eventually clearing the waste chamber 123.

After washing, the assay tube 140 and inert support 141 will be free of unbound labeled reagent so that only bound labeled reagent will be detected.

After completion of the washing operation, the washed tubes are transferred to a detection station for quantification of the analyte of interest, such as by chemiluminescent techniques described in U.S. Pat. No. 5,316,726, which is incorporated herein by reference.

The use of the tube washing system 110, such as shown in FIG. 4, greatly facilitates the washing operation required in performing an immunoasssay and represents a significant improvement over the use of aspiration equipment in an automated immunoassay analyzer environment. In particular, removal of the sample and wash fluid in the above-described manner allows the wash operation to be performed rapidly and facilely.

The inert supports with bound biomaterial on a surface thereof referred to herein, are analytical elements previously added to the assay tubes that are washable by the tube washing system of the invention. The analytical elements preferably are biomaterial coated beads (e.g., about 0.25 inch diameters) used as the solid phase for heterogenous immunoassays to quantitate analytes in solution. One bead is consumed for each test conducted, and a particular type of bead can be used for any number of different assay types, depending on the reagent used therewith.

The biomaterial coated beads themselves comprise an inert substrate, such as plastic, having a surface, wherein a biomaterial is bound to said surface. The biomaterial generally is selected from an antigen or an antibody. For example, the invention will support the following test categories: thyroid function, sex hormones, growth hormones, tumor markers, infectious diseases, allergy testing, immunoglobin and related proteins and peptides, steroids and other small molecules, therapeutic drugs, drugs of abuse, and vitamins. The immunological chemistries can be processed in any of the following formats: competition assays, sandwich assays, and liquid phase capture assays.

An analyzer using the tube washing system of the present invention represents a high throughput automated system capable of assaying a broad range of chemicals, or biofluids such as analytes in serum, plasma, and urine. It is also contemplated within the scope of the invention that specific chemistry kits might also handle clarified cerebrospinal fluid or saliva. The system imparts a high degree of automation to a diverse set of immunoassays, such as encountered in hospital and commercial laboratory settings. As such, high volume testing (up to even 200 tests results per hour) is expected and must be accommodated. In addition, the urgency of medical decisions that will depend on the results of these assays dictates a rapid analytical response time.

While the invention has been described in terms of its preferred embodiments, those skilled in the art will recognize that the invention can be practiced with modification within the spirit and scope of the appended claims.

We claim:

1. A tube washing system, comprising:
   a tube spinning station having
      a rotatable chuck, wherein said chuck comprises a body portion and a plurality of spaced apart teeth defining intervening grooves extending through said body portion with at least one of said grooves permitting passage of fluid through said body portion and at least one other of said grooves providing means to receive and mechanically connect a projection on an open end of a tube,
      a fluid waste chamber housing said chuck, and said waste chamber comprises means to collect and drain fluid, and an aperture defined in a lower side of said chamber having a size effective to permit entry of said tube into said chamber,
      a pipette for dispensing wash water into said tube, said pipette located centrally within said chuck,
      drive means to rotate said chuck; and
   a tube elevating means located beneath said tube spinning station, said tube elevating means comprising a freely rotatable tube holder, and lifting means provided to vertically move said tube holder towards and away from said chuck.

2. The tube washing system of claim 1, further comprising said tube mechanically interlocked with said chuck for co-rotation, wherein said tube comprises at least one vertically extending, lineal ridge provided on the inner surface of said tube, wherein said at least one ridge being of a size permitting sliding into and mating of said at least one ridge with said at least one chuck groove effective to provide a means of temporarily physically interlocking said tube and said chuck for joint rotation.

3. A method of washing a tube, comprising:
   (a) providing a tube spinning station having;
      a rotatable chuck, wherein said chuck comprises a body portion and a plurality of spaced apart teeth defining intervening grooves extending through said body portion with at least one of said grooves permitting passage of fluid through said body portion and at least one other of said grooves providing means to receive and mechanically connect to one of a plurality of projections provided on an open end of a tube,
      a fluid waste chamber housing said chuck, and said waste chamber comprises means to collect and drain fluid, and an aperture defined in a lower side of said chamber having a size effective to permit entry of said tube into said chamber,
      a pipette for dispensing wash water into said tube, said pipette located centrally within said chuck, and
      spin drive means to rotate said chuck;
   (b) providing a tube elevating means located beneath said tube spinning station, said tube elevating means comprising a freely rotatable tube holder, and lift drive means provided to vertically move said tube holder towards and away from said chuck;
   (c) providing said tube, wherein said tube contains a fluid;

(d) vertically lifting said tube containing said fluid with said tube elevating means by said lift drive means until at least one of said projections provided on said open end of said tube slides into and mates with said at least one other of said chuck grooves; and (e) driving said chuck in rotation by said spin drive means, thereby expelling fluids from said tube into said waste chamber through unmated grooves in said chuck.

4. The method of claim 3, further comprising:

(f) dispensing wash water into said tube via said pipette;

(g) driving said chuck in rotation by said spin drive means, thereby expelling said wash water from said tube into said waste chamber through said grooves in said chuck; and (h) optionally repeating steps (f) and (g) at least one more time.

5. The method of claim 4, further comprising:

(i) discontinuing said driving of said chuck in rotation;

(j) vertically lowering said tube with said tube elevating means by reversing said lift drive means until said at least one projection slides out of said at least one chuck groove and said tube leaves said waste chamber.

6. The method of claim 3, wherein said tube provided in step (c) further comprises an inert support onto which a biomaterial is bound.

7. The method of claim 6, wherein said biomaterial is selected from the group consisting of an antigen and an antibody.

8. The method of claim 3, wherein said tube provided in step (c) further contains an inert support having a surface, wherein said inert support comprises a bead having a biomaterial coated on said surface, and said inert support is retained inside said tube upon the completion of step (e).

9. The method of claim 8, wherein said biomaterial is selected from the group consisting of an antigen and an antibody.

* * * * *